(12) United States Patent
Furukawa et al.

(10) Patent No.: US 7,919,759 B2
(45) Date of Patent: Apr. 5, 2011

(54) CHARGED PARTICLE BEAM IRRADIATOR AND ROTARY GANTRY

(75) Inventors: Takuji Furukawa, Chiba (JP); Kouji Noda, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 212 days.

(21) Appl. No.: 11/792,940

(22) PCT Filed: Oct. 31, 2005

(86) PCT No.: PCT/JP2005/019967
§ 371 (c)(1),
(2), (4) Date: Jun. 13, 2007

(87) PCT Pub. No.: WO2006/064613
PCT Pub. Date: Jun. 22, 2006

(65) Prior Publication Data
US 2008/0006776 A1    Jan. 10, 2008

(30) Foreign Application Priority Data
Dec. 13, 2004    (JP) .................................. 2004-359325

(51) Int. Cl.
*H01J 1/50* (2006.01)
(52) U.S. Cl. ............................. 250/396 ML; 250/396 R
(58) Field of Classification Search .................... None
See application file for complete search history.

(56) References Cited

U.S. PATENT DOCUMENTS

| | | | | |
|---|---|---|---|---|
| 4,687,936 A * | 8/1987 | McIntyre et al. | ............. | 250/397 |
| 4,726,046 A * | 2/1988 | Nunan | ............................ | 378/65 |
| 4,767,930 A * | 8/1988 | Stieber et al. | .......... | 250/396 ML |
| 5,349,198 A * | 9/1994 | Takanaka | .................... | 250/492.3 |
| 5,481,116 A * | 1/1996 | Glavish et al. | .......... | 250/396 ML |
| 5,760,395 A * | 6/1998 | Johnstone | ........................ | 850/62 |
| 6,034,377 A * | 3/2000 | Pu | .............................. | 250/492.3 |
| 6,218,675 B1 * | 4/2001 | Akiyama et al. | ............ | 250/492.3 |

(Continued)

FOREIGN PATENT DOCUMENTS

EP    1041579 A1 * 10/2000

(Continued)

OTHER PUBLICATIONS

Timothy R. Renner, et al., An abstract of "Wobbler Facility for Biomedical Experiments", Medical Physics, vol. 14, Issue 5, Sep. 1987, pp. 825-834.

*Primary Examiner* — Bernard E Souw
*Assistant Examiner* — Andrew Smyth
(74) *Attorney, Agent, or Firm* — Squire, Sanders & Dempsey (US) LLP

(57) ABSTRACT

A charged particle beam 2 which enters a final bending electromagnet 7 after traveling through quadrupole electromagnets 4, 5, 6 travels through the final bending electromagnet 7 in an arc shape path by increasing or decreasing a bending magnetic field generated in the final bending electromagnet 7, with a pre-determined period for example and is scanned in an X-direction. The charged particle beam 2 scanned in the X-direction is scanned in a Y-direction while traveling through a Y-direction Wobbler electromagnet 8. Consequently, the charged particle beam 2 is scanned in the X-direction and the Y-direction, and the target 9 is irradiated with the charged particle beam 2 so that a round field is drawn, for example.

2 Claims, 4 Drawing Sheets

U.S. PATENT DOCUMENTS

| | | | |
|---|---|---|---|
| 6,476,403 B1 * | 11/2002 | Dolinskii et al. | 250/492.3 |
| 6,534,766 B2 * | 3/2003 | Abe et al. | 250/307 |
| 6,683,318 B1 * | 1/2004 | Haberer et al. | 250/492.3 |
| 6,693,283 B2 * | 2/2004 | Eickhoff et al. | 250/396 ML |
| 6,750,462 B2 * | 6/2004 | Iwasawa et al. | 250/492.3 |
| 6,800,862 B2 * | 10/2004 | Matsumoto et al. | 250/492.21 |
| RE40,009 E * | 1/2008 | Olson et al. | 250/492.21 |
| 7,375,354 B2 * | 5/2008 | Iwasawa et al. | 250/492.21 |
| 7,531,818 B2 * | 5/2009 | Brahme | 250/492.1 |
| 2001/0042841 A1 * | 11/2001 | Lyons et al. | 250/492.3 |
| 2004/0113094 A1 * | 6/2004 | Lyons et al. | 250/435 |
| 2007/0131876 A1 * | 6/2007 | Brahme | 250/492.1 |

FOREIGN PATENT DOCUMENTS

| | | |
|---|---|---|
| JP | 08-257148 | 8/1996 |
| JP | 8-257148 | 10/1996 |
| JP | 3423675 | 1/2002 |
| JP | 3423675 | 7/2003 |
| JP | 2003-339891 | 12/2003 |
| JP | 2004-167136 | 6/2004 |

* cited by examiner

CHARGED PARTICLE BEAM IRRADIATOR AND ROTARY GANTRY

TECHNICAL FIELD

The present invention relates to a charged particle beam irradiator and a rotary gantry, for treating a cancer by irradiating cancer cells of a patient with a charged particle beam, for example.

BACKGROUND ART

Conventionally, for treating a cancer by a radiation ray, an X-ray, a gamma ray and an electron beam, etc., have been applied, and in recent years, a charged particle beam irradiator which treats a cancer, etc., using a high energy charged particle beam (such as a carbon ion beam, etc.,) accelerated by an accelerator has been developed (refer to non-patent document 1).

Here, a description is given on a charged particle beam irradiator 100 as described above, referring to FIG. 4 and FIG. 5. As illustrated in FIG. 4, charged particles which are accelerated with high energy while traveling through an accelerator (not illustrated) such as a synchrotron, etc., enter a final bending electromagnet, after traveling through quadrupole electromagnets 110, 111, 112, etc. The quadrupole electromagnets 110, 111, 112 are converging electromagnets which suppress the divergence of the beam traveling through a beam transfer tube 114, and the final bending electromagnet bends charged particles toward a target. Then, the charged particles which enter the final bending electromagnet 113 travel in the bending electromagnet 113 drawing a curve in an arc shape.

Next, as illustrated in FIG. 4 and FIG. 5, the charged particle beam travels through an X-direction dipole electromagnet (an irradiation field forming electromagnet) 115 which scans the beam in the X-direction which is parallel to a plane including a bending trajectory of the beam traveling through the final bending electromagnet 113 and being perpendicular to the direction of the beam traveling, and further travels through a Y-direction dipole electromagnet (an irradiation field forming electromagnet) 116 which scans the beam in the Y-direction being perpendicular to the direction of the beam traveling and the X-direction, and then a target 117 is irradiated with the charged particle beam. Otherwise, a configuration is possible where the charged particle beam travels through an X-direction dipole electromagnet after traveling through a Y-direction dipole electromagnet.

Meanwhile, in treating a cancer using such a charged particle beam irradiator 100, 180 degree—or 360 degree—rotation irradiation centering around the cancer cells is preferable, in order to increase an efficiency of the cancer treatment and to relieve the patient from pain. Accordingly, if a charged particle beam is applied in cancer treatment, a rotary gantry which irradiates a patient lying on a bed with a proton beam from the circumference is used widely (refer to patent document 1).

Non-patent document 1: 'Wobbler facility for biological experiments' Timothy R. Renner and William T. Chu, Medical Physics, Vol. 14, pp. 825-834 (1987)

Patent document 1: Japanese Laid Open Patent Application Publication No. 1996-257148 (paragraphs 0012-0013 and FIG. 1).

Meanwhile, in a conventional charged particle beam irradiator 100, two dipole electromagnets of an X-direction dipole electromagnet 115 and a Y-direction dipole electromagnet 116 are disposed in a downstream side of a final bending electromagnet 113. Here, the X-direction dipole electromagnet 115 and Y-direction dipole electromagnet 116 are required to generate an electromagnetic field larger by a factor of three than an electromagnetic field applied for bending a proton beam, because ions such as a carbon ion, etc., are heavier than proton. Further, for treating a cancer, etc., the charged particle beam with a diameter of about 1 cm supplied from an accelerator is required to be enlarged to a size which can form an irradiation field of about 20 cm in diameter. Therefore, in order to enlarge a charged particle beam composed of a carbon ion beam, etc., using the X-direction and the Y-direction dipole electromagnets, a length of irradiating port (a length between either the X-direction dipole electromagnet 115 or the Y-direction dipole electromagnet 116 disposed in an upstream side and the target 117), is needed to be lengthened further. If a charged carbon beam (a carbon ion beam) is applied, a rather long port length around 5.5 m is needed at the shortest, and thereby, a problem that the apparatus gets bigger is raised.

If the charged particle beam irradiator as described above is applied to a rotary gantry described in patent document 1, a space needed for driving the rotary gantry should be about $18 \times 9 \times 9 \times \pi$ m$^3$, for example, and thereby, a problem that the apparatus gets bigger is raised.

Accordingly, a charged particle beam irradiator and a rotary gantry which come in a reduced size as a whole have been desired.

DISCLOSURE OF INVENTION

The present invention relates to a charged particle beam irradiator which includes a bending electromagnet which bends a charged particle beam accelerated by an accelerator toward a target, and an irradiation field forming electromagnet which scans the charged particle beam travels through the bending electromagnet and irradiates a field on the target, wherein the bending electromagnet bends the charged particle beam as described, and scans the beam in an X-direction which is parallel to a plane including a bending trajectory of the beam and being perpendicular to a direction of the beam traveling and further the irradiation field forming electromagnet scans the beam in a Y-direction which is perpendicular to the direction of the beam traveling and the X-direction.

According to the present invention, the charged particle beam which enters the bending electromagnet can be scanned in the X-direction parallel to a plane including the bending trajectory of the beam and being perpendicular to the direction of the beam traveling, through controlling the bending electromagnetic field. Accordingly, the bending electromagnet can be used as an electromagnet having the same function as the irradiation field forming electromagnet which scans the beam in the X-direction, and thereby, a length of an irradiating port can be shortened because it is unnecessary to install the irradiation field electromagnet in addition to the bending electromagnet.

Further, the present invention relates to a rotary gantry including the charged particle beam irradiator.

According to the present invention, a rotary gantry in which an irradiation field forming electromagnet which scans the beam in the X-direction is omitted can be assembled, and a length of irradiating port can be shortened. Resultantly, a rotating radius of the rotary gantry can be made smaller, and a size of the rotary gantry can be reduced.

As described above in detail, according to the present invention, the size of the whole apparatus can be reduced, because a point which is an origin of the beam being scanned can be disposed in the bending electromagnet. Because the irradiation field forming electromagnet which scans the beam in the X-direction can be omitted, the size of the whole apparatus can be reduced further, thereby.

BEST MODES FOR CARRYING OUT THE INVENTION

First Embodiment

Figure 1:
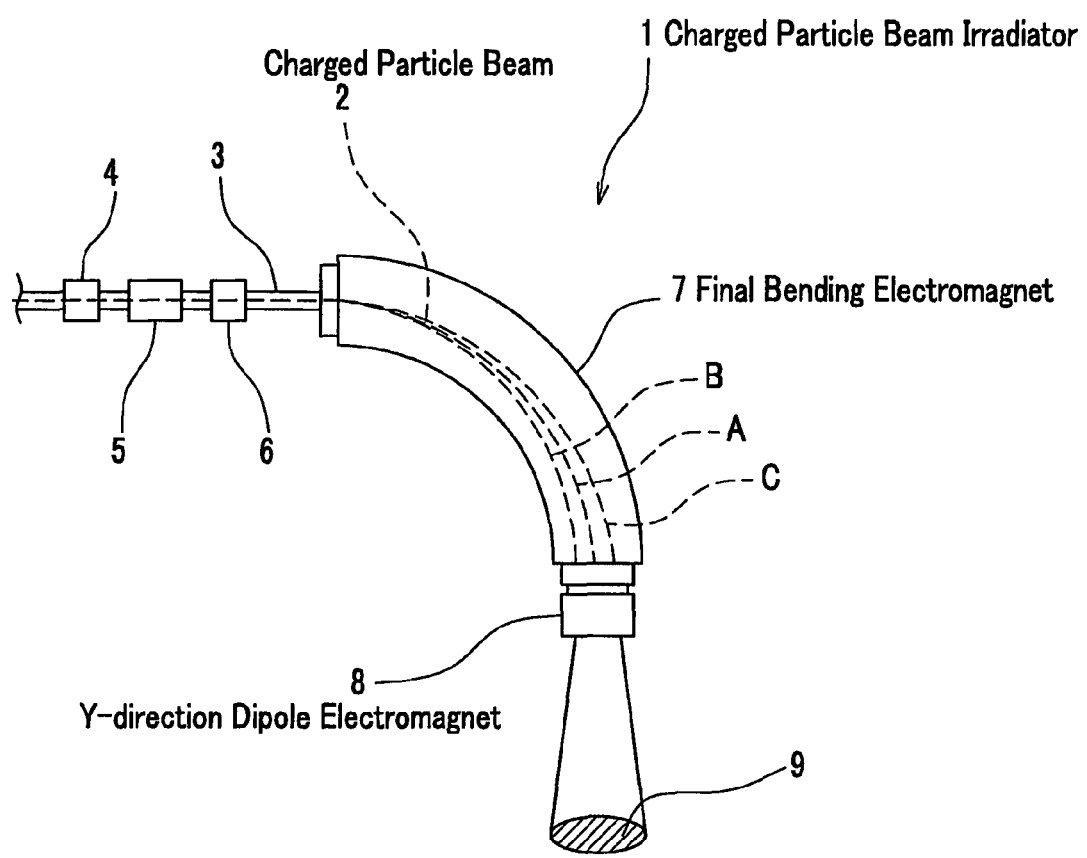
FIG. 1 is a drawing illustrating an assembly of an irradiating portion of a charged particle beam irradiator according to a first embodiment of the present invention.
Figure 2:
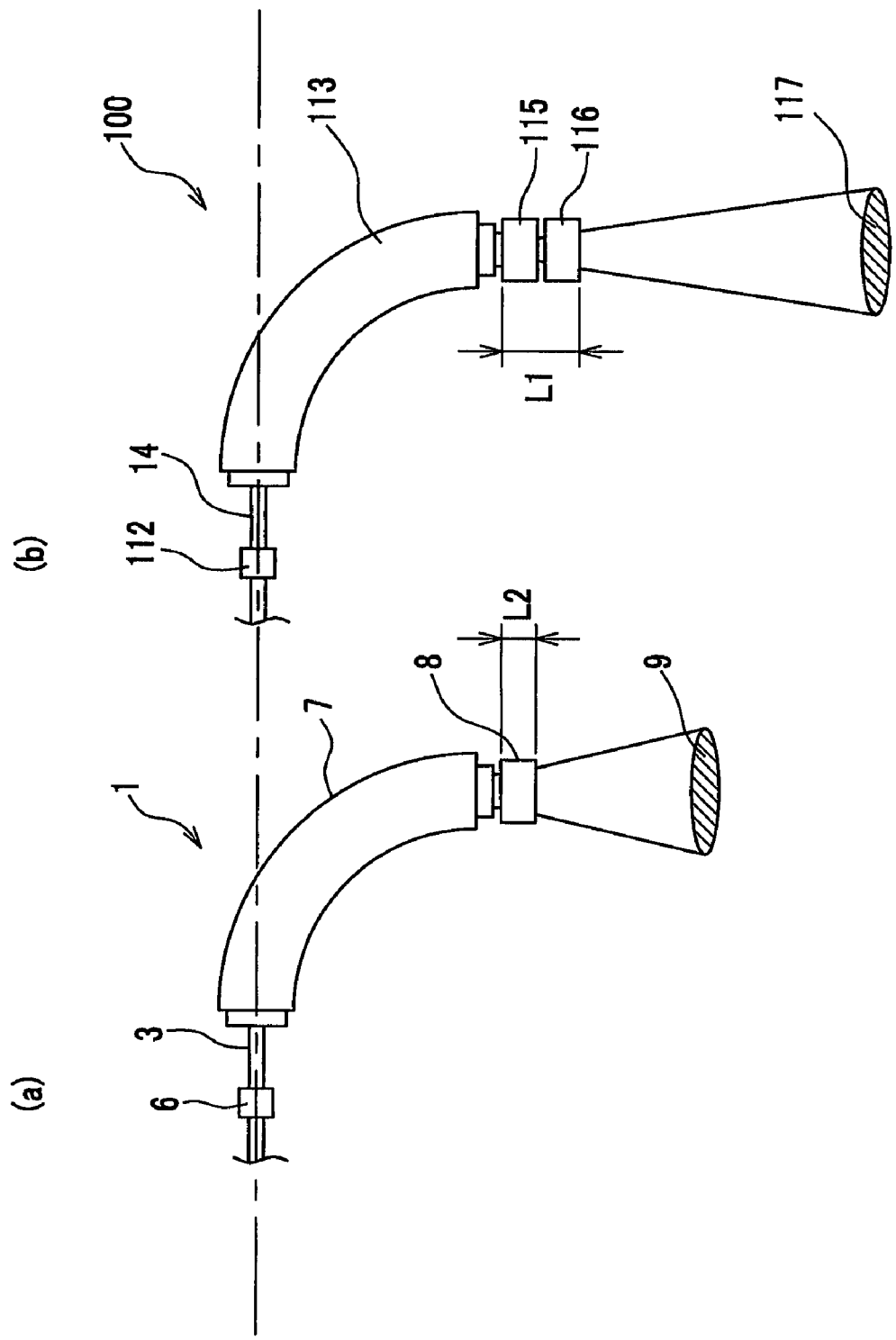
FIG. 2 compares a charged particle beam irradiator according to the first embodiment of the present invention and a charged particle beam irradiator according to a conventional art, wherein, (a) shows a charged particle beam irradiator according to the first embodiment, and (b) shows a charged particle beam irradiator according to a conventional art.

A description is given, referring to the attached drawings FIG. 1 and FIG. 2, on a charged particle beam irradiator according to the first embodiment of the present invention. FIG. 1 is a drawing illustrating an assembly of an irradiating portion of a charged particle beam irradiator according to the present embodiment. FIG. 2 compares a charged particle beam irradiator according to the present embodiment and a charged particle beam irradiator according to a conventional art, wherein (a) shows the charged particle beam irradiator according to the present embodiment, and (b) shows a charged particle beam irradiator according to the conventional art.

Figure 4:
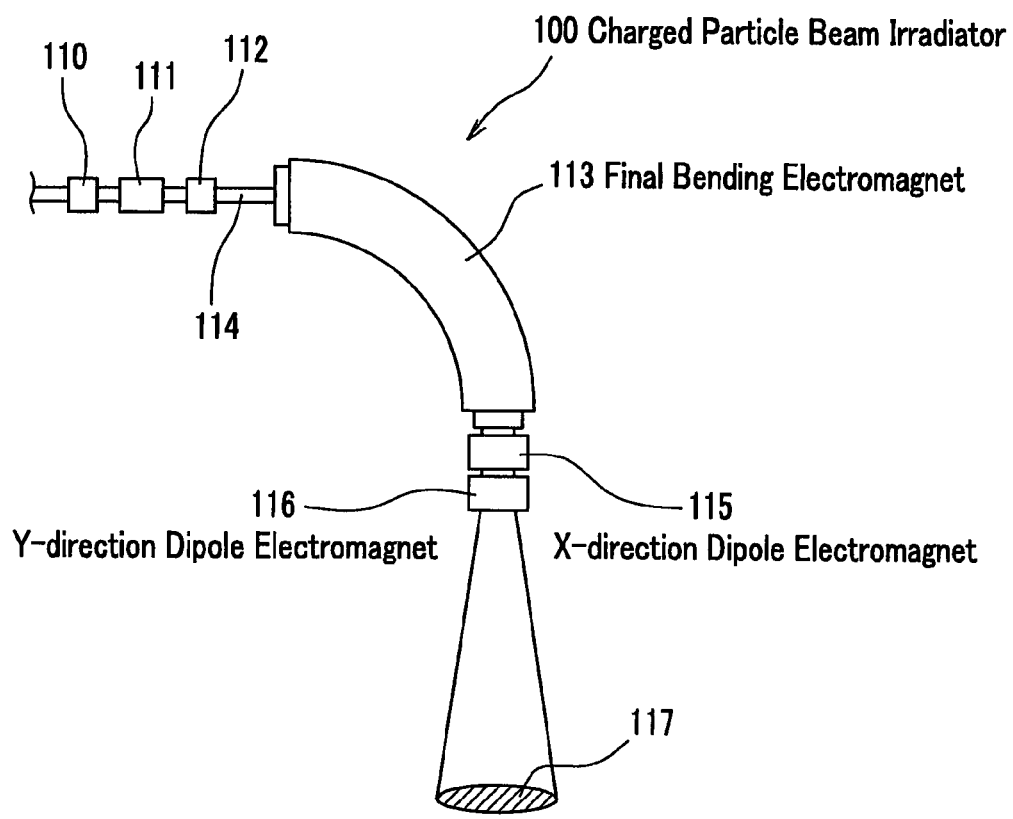
FIG. 4 is a drawing illustrating an assembly of an irradiating portion of a charged particle beam irradiator according to a conventional art.
Figure 5:
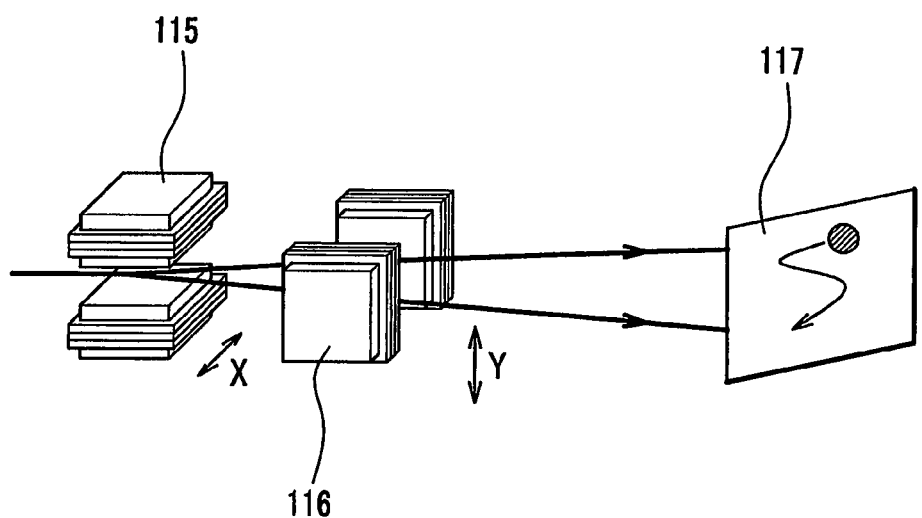
FIG. 5 is an enlarged perspective view showing an X-direction irradiation field forming electromagnet and a Y-direction irradiation field forming electromagnet according to a conventional art.

As illustrated in FIG. 1, in the same way as described in the description of the background art on the charged particle beam irradiator 100, the charged particle beam irradiator 1 includes a beam transfer tube 3 through which a charged particle beam such as a carbon ion beam, etc., travels; quadrupole electromagnets 4, 5, 6 which are disposed in the beam transfer tube 3 and converge the charged particle beam 2; a final bending electromagnet 7 which is connected to a downstream side end of the beam transfer tube 3; and a Y-direction dipole electromagnet (an irradiation field forming electromagnet) 8 which is connected to a downstream side end of the final bending electromagnet 7. However, according to the present embodiment, an X-direction dipole electromagnet 115 (refer to FIG. 4) described in the description of the background art is omitted, and so, the configuration is different between the first embodiment and the conventional art. Here, as described in the description of the background art, the X-direction means a direction which is parallel to a plane including a bending trajectory of the beam bent by the final bending electromagnet 7 and being perpendicular to a direction of the beam traveling. Meanwhile, the Y-direction means a direction which is perpendicular to the direction of the beam traveling and the X-direction.

Here, the final bending electromagnet 7 changes the trajectory of the charged particle beam 2 to an arc shape by generating a bending magnetic field in the final bending electromagnet 7, and scans the charged particle beam 2 in the X-direction by increasing or decreasing the bending electromagnetic field with a pre-determined period, for example. For example, as illustrated in FIG. 1, one beam bended along the bending trajectory of a dotted line A is scanned inward in the X-direction to the position of the dotted line B at the maximum, and is scanned outward in the X-direction to the position of the dotted line C at the maximum, by increasing or decreasing the bending electromagnetic field, as described above. In other words, one beam is scanned in the X-direction between the dotted line B and the dotted line C. The Y-direction dipole electromagnet 8 scans the charged particle beam 2 in the Y-direction perpendicular to the X-direction.

Next, a description is given on the operation of the charged particle beam irradiator 1 configured as described above. Firstly, the charged particle beam 2 which enters the final bending electromagnet 7 after traveling through the quadrupole electromagnets 4, 5, 6, travels therein along an arc shaped trajectory and is scanned in the X-direction, as shown by the dotted lines in FIG. 1, by increasing or decreasing the bending electromagnetic field generated in the final bending electromagnet 7 with a pre-determined period. Then, the charged particle beam 2 which is scanned in the X-direction, is scanned in the Y-direction perpendicular to the X-direction, while traveling through the Y-direction dipole electromagnet 8. Accordingly, the charged particle beam 2 is scanned in the X-direction and the Y-direction, and a target 9 which is an affected part of a patient is irradiated with the charged particle beam 2, uniformly and without any miss-scanned part being formed, following a pre-determined program pre-set for the target 9.

Accordingly, because the X-direction dipole electromagnet 115 can be omitted in the charged particle beam irradiator 1 where the final bending electromagnet 7 performs also a function of the X-direction dipole electromagnet 115 according to a conventional art, the whole size of the charged particle beam irradiator 1 can be reduced by a dimension L (L=L1−L2=about 1 m), and the size of the charged particle beam irradiator 1 can be reduced.

Second Embodiment

Figure 3:
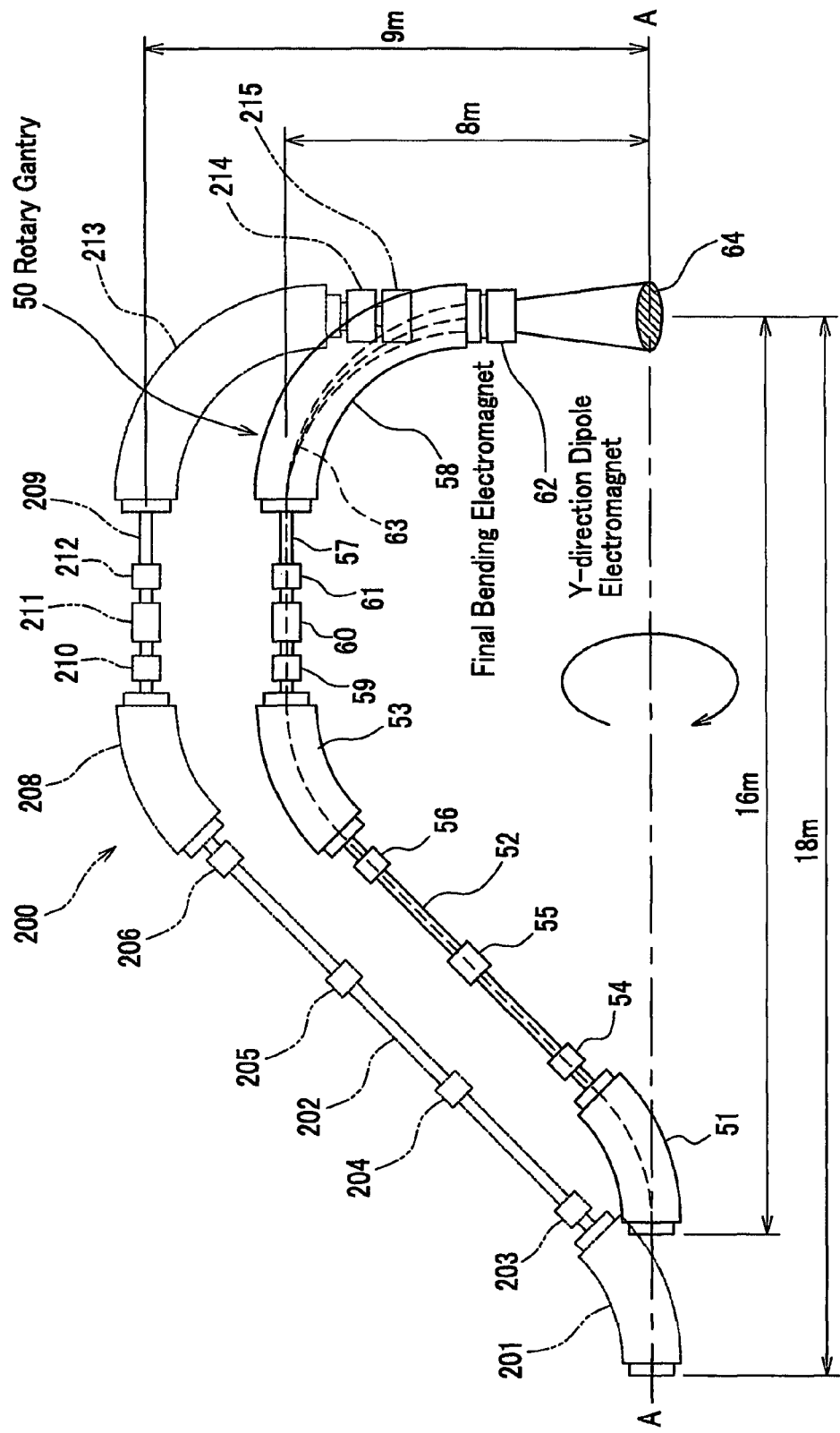
FIG. 3 compares a rotary gantry according to a second embodiment of the present invention and a rotary gantry according to a conventional art.

Next, FIG. 3 illustrates a second embodiment according to the present invention. FIG. 3 compares a rotary gantry according to the present embodiment and a rotary gantry according to a conventional art.

As illustrated in FIG. 3, the rotary gantry 50 includes a first bending electromagnet 51; a second bending electromagnet 53 which is connected to the first bending electromagnet 51 through a beam transfer tube 52; quadrupole electromagnets 54, 55, 56 installed along the beam transfer tube 52; a third bending electromagnet (final bending electromagnet, hereinafter) 58 which is connected to the second bending electromagnet 53 through a beam transfer tube 57; quadrupole electromagnets 59, 60, 61 installed along the beam transfer tube 57; and a Y-direction dipole electromagnet 62 which is connected to a downstream side end of the final bending electromagnet 58.

Meanwhile, as illustrated by virtual lines in FIG. 3, a rotary gantry 200 according to the conventional art includes a first bending electromagnet 201; a beam transfer tube 202; quadrupole electromagnets 203, 204, 205, 206, a second bending electromagnet 208; a beam transfer tube 209; quadrupole electromagnets 210, 211, 212; a third bending electromagnet 13; an X-direction dipole electromagnet 214; and a Y-direction dipole electromagnet 215.

In the rotary gantry 50 according to the present embodiment which is configured as described above, a charged particle beam 63 accelerated with high energy while traveling through an accelerator (not illustrated) such as a synchrotron, etc., enters the final bending electromagnet 58, after traveling through the first bending electromagnet 51, the quadrupole electromagnets 54, 55, 56, the second bending electromagnet 53 and quadrupole electromagnets 59, 60, 61, in turn. The charged particle beam 63 which enters the final bending electromagnet 58 travels in the final bending electromagnet 58 in an arc shape and is scanned in the X-direction, by controlling to increase or to decrease the bending electromagnetic field generated in the final bending electromagnet 58 with a predetermined period, for example. Then, the charged particle beam 63 which is scanned in the X-direction, is scanned in a Y-direction, while traveling through the Y-direction dipole electromagnet 62. Consequently, the charged particle beam 63 is scanned in the X-direction and the Y-direction, while traveling through the Y-direction dipole electromagnet, and the target 64 which is an affected part of a patient is irradiated with the charged particle beam 63 so that a round field is drawn, for example.

Then, the rotary gantry 50 is designed so as to rotate 360 degrees along the circumference of the target 64, centering on the rotation axis A-A which connects the final bending electromagnet 58 and the target 64, using a drive motor (not illustrated), etc. That is, the rotary gantry 20 can irradiate the target 64 at any angle of surrounding 360 degrees, wherein an irradiating port 65 from which emitted charged heavy particles are emitted rotates around the target 64.

In the second embodiment configured as described above, because the X-direction dipole electromagnet 214 according to a conventional art can be omitted in the rotary gantry 50 where the final bending electromagnet 58 performs also a function of the X-direction dipole electromagnet 214 in the same way as described in the first embodiment, the size of the rotary gantry 50 can be reduced by dimensions corresponding to the size of the X-direction dipole electromagnet 214. Further, as illustrated in FIG. 3, while a space necessary for operating a rotary gantry 50 according to a conventional art is about 18×9×9×π m³ for example, the space can be reduced to about 16×8×8×π m³ for example and thereby the space for installing the rotary gantry 50 can be reduced in the present embodiment.

Meanwhile, because the size of the rotary gantry 50 can be reduced, a total length of the beam transfer tube 52 can be reduced to a length shorter than a total length of the beam transfer tube 202 according to the conventional art. Generally, the quadrupole electromagnets 203, 204, 205, 206 are placed at even intervals along the beam transfer tube 202. Accordingly, because the total length of the beam transfer tube 52 can be reduced to a length shorter than the total length of the beam transfer tube 202 according to the conventional art, the number of quadrupole electromagnets necessary is reduced to three corresponding to the quadrupole electromagnets 54, 55, 56 along the beam transfer tube 52 in the present embodiment, from four corresponding to the quadrupole electromagnets 203, 204, 205, 206 along the beam transfer tube 202 in the conventional art, and thereby, the size of the rotary gantry can be reduced further, and due to a resultant reduction of the rotation moment, manufacturing cost of the rotary gantry 50 can be reduced.

While, in the first embodiment, one piece of the Y-direction dipole electromagnet 8 is disposed in the downstream side of the final bending electromagnet 7, the present invention is not limited to the content of the first embodiment. One piece of the X-direction dipole electromagnet can be disposed at a position between the final bending electromagnet 7 and the Y-direction dipole electromagnet 8. The same condition holds for the second embodiment.

The invention claimed is:

1. A charged particle beam irradiator irradiating a target with a charged particle beam accelerated by an accelerator, comprising:
    a bending electromagnet for bending the charged particle beam toward the target; and
    an irradiation field forming electromagnet for irradiating the target by scanning the charged particle beam which travels through the bending electromagnet,
    wherein, the bending electromagnet first scans the charged particle beam in an X-direction which is parallel to a plane including a bending trajectory of the beam and being perpendicular to a direction of the charged particle beam traveling by increasing or decreasing the bending electromagnetic field; and
    the irradiation field forming electromagnet subsequently scans the charged particle beam in a Y-direction which is perpendicular to the direction of the beam traveling and the X-direction of the charged particle beam, whereby irradiating the target with the charged particle beam is performed.

2. A rotary gantry comprising the charged particle beam irradiator according to claim 1.

* * * * *